United States Patent [19]

Volkov et al.

[11] 4,006,740
[45] Feb. 8, 1977

[54] SURGICAL APPARATUS FOR EXTERNAL TRANSOSTEAL FIXATION OF BONE FRAGMENTS AND JOINT ENDS

[76] Inventors: Mstislav Vasilievich Volkov, 1 Stroitelnaya ulitsa 6, kor. 1, kv. 63; Oganes Vardanovich Oganesian, ulitsa Pervomaiskaya, 74, kv. 87, both of Moscow, U.S.S.R.

[22] Filed: July 8, 1975

[21] Appl. No.: 593,976

[30] Foreign Application Priority Data

July 22, 1974  U.S.S.R. ............................ 2052127

[52] U.S. Cl. .............................. 128/84 B; 128/92 A
[51] Int. Cl.² .......................................... A61F 5/04
[58] Field of Search ................ 128/84 B, 84 R, 83, 128/92 R, 92 A, 92 B, 92 E

[56] References Cited

UNITED STATES PATENTS

| | | | |
|---|---|---|---|
| 2,035,952 | 3/1936 | Ettinger | 128/84 B |
| 2,055,024 | 9/1936 | Bittner, Jr. | 128/92 A |
| 2,101,889 | 12/1937 | Anderson | 128/84 B |
| 2,120,446 | 6/1938 | Thomas | 128/84 B |
| 2,238,870 | 4/1941 | Haynes | 128/92 A |
| 2,391,537 | 12/1945 | Anderson | 128/84 B |
| 2,760,488 | 8/1956 | Pierce | 128/92 A |

*Primary Examiner*—John D. Yasko
*Attorney, Agent, or Firm*—Steinberg & Blake

[57] ABSTRACT

A surgical apparatus for external transosteal fixation of bone fragments and joint ends comprises needles to be driven through the bones being aligned which are secured in braces. The braces are provided with means for fixing and tightening the needles, said means being formed as drive screws cooperating with turn-buckle nuts. There are through axial holes for needles formed in the drive screws, and the tips of the needles extended through said holes are provided with bulges larger in diameter than said holes. The apparatus ensures secure fixation of the needles with a prescribed degree of tension, the latter parameter lending itself to correction in the course of treatment.

4 Claims, 12 Drawing Figures

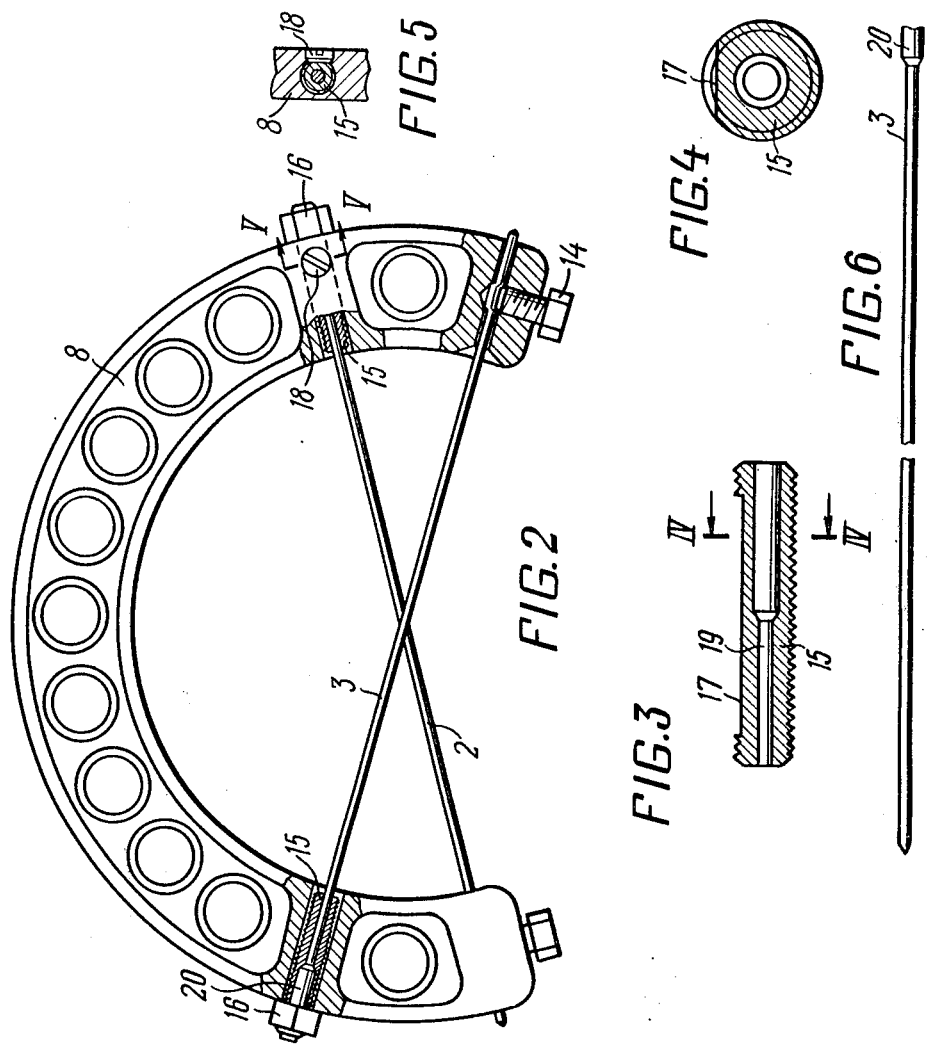

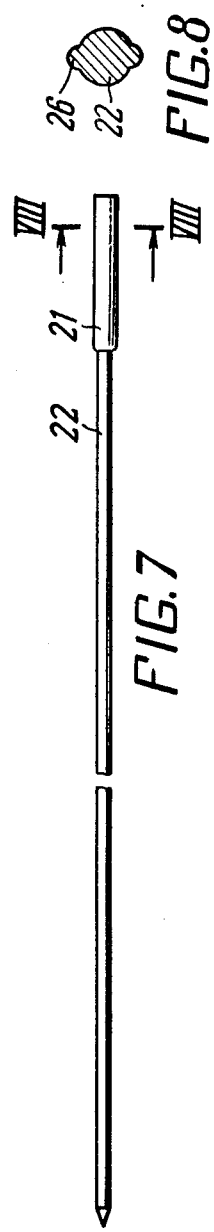

SURGICAL APPARATUS FOR EXTERNAL TRANSOSTEAL FIXATION OF BONE FRAGMENTS AND JOINT ENDS

The present invention relates to medical equipment and more specifically to surgical apparatus for external transosteal fixation of bone fragments and joint ends.

The apparatus of this invention may find use in orthopaedics and traumatology for secure fixation of bone fragments and joint ends in the compression or distraction posititions required in the surgical therapy of bones and joints.

It is widely known in the art to employ surgical apparatus for external transosteal fixation of bone fragments and joint ends, which comprise two or more pairs of needles, the tips of the needles of each pair being so secured in a traumatological brace or two rigidly interconnected braces that each pair of needles forms a rigid system with the brace. The needles of each rigid system are driven through one of the bones being aligned. Said rigid systems are interconnected by means of distractors enabling the distance between said systems to be varied and their layout to be changed. Should the apparatus be employed for treating bone fractures, the distractors are rigidly coupled to the braces; whereas if the apparatus is employed for treating joints, the distractors are rigidly coupled to one rigid system constituted by said needles and braces and connected to the other rigid system by means of an articulated joint simulating the joint movement.

The needles are secured in the braces with the aid of holes through which are extended the tips of the needles which are secured in the holes by means of set screws. However, this type of fastening in the known apparatus hampers the task of adjusting the degree of tension of the needles and inconveniences the surgeon applying the apparatus.

It is likewise known in the art to employ a surgical apparatus for external transosteal fixation of joint ends, in which the needles have threaded tips secured in seats formed in the braces and accommodating self-adjusting hollow cylindrical inserts. Said inserts accommodate sleeve nuts whereinto the needles are screwed. (cf. USSR Inventor's Certificate No. 310,655).

It is likewise known in the art to employ a surgical apparatus for external transosteal fixation of joint ends, in which the needles have threaded tips and there are seats formed in the braces which accommodate self-adjusting hollow cylindrical inserts, said inserts accommodating sleeve nuts into which the needles are screwed.

Having been driven through the bone, the tips of the needles are guided into the cylindrical inserts of the brace, the sleeve nuts are screwed thereon, and the sleeve nuts are tightened with the aid of a socket wrench to a prescribed degree of needle tension.

The latter known apparatus has the following disadvantages: its braces are too intricate a design difficult to manufacture and operate; the thread on the needle is likely to be stripped in case of overtension; the apparatus cannot employ thin needles. All said disadvantages limit the scope of application of the prior art apparatus.

It is an object of the invention to provide a surgical apparatus for external transosteal fixation of bone fragments and joint ends of such a design as would provide for secure fixation of the needle in the braces thereof.

It is another object of the invention to provide an apparatus which would make it possible to achieve a prescribed degree of needle tension in the course of therapy as well as to correct the degree of needle tension by a simple procedure, if same should be required.

It is yet another object of the invention to provide an apparatus simple in design and easy to manufacture.

It is a further object of the invention to provide an apparatus lending itself to a simpler application procedure.

The foregoing and other objects are attained by that in a surgical apparatus for external transosteal fixation of bone fragments and joint ends comprising needles to be driven through the bones being aligned which are fastened to the ends of braces interconnected by means of distractors serving to provide for a desired layout of the braces with the needles, in accordance with the invention, the braces are provided with means for fixing and tightening the needles formed as drive screws accommodated in seats provided in the braces and cooperating with turn-buckle nuts, said drive screws being provided with external flats cooperating with set screws which prevent said drive screws from turning in the seats of the braces, and said drive screws having through axial holes formed therein through which the needles are to be extended, while the tips of the needles extended through said axial holes are provided with bulges larger in diameter than said axial holes.

The bulges on the tips of the needles may be formed as lateral projections, in which case the axial holes formed in the drive screws must be provided with through side slots corresponding in shape and cross-sectional dimension to said lateral projections.

The proposed surgical apparatus provides for secure fixation of the bones being aligned, jerk-free tightening of the needles and a possibility of maintaining or varying the degree of needle tension in the course of therapy, by an elementary procedure. The apparatus of this invention takes less time to be applied than the prior art apparatus.

The invention will be further understood from the following description of exemplary embodiments thereof taken in conjunction with the accompanying drawings, wherein:

FIG. 2 illustrates one of the braces of the proposed apparatus, in accordance with the invention;

FIG. 3 shows the drive screw of the proposed apparatus, in accordance with the invention;

FIG. 4 is a sectional view taken on the line IV—IV in FIG. 3;

FIG. 5 is a sectional view taken on the line V—V in FIG. 2;

FIG. 6 illustrates the needle of the proposed apparatus, in accordance with the invention;

FIG. 7 illustrates an alternative embodiment of the needle of the proposed apparatus, in accordance with the invention;

FIG. 8 is a sectional view taken on the line VIII—VIII in FIG. 7;

FIG. 9 illustrates the way the needle shown in FIG. 7 is secured in the drive screw of the apparatus, in accordance with the invention;

FIG. 10 illustrates the drive screw of the proposed apparatus for securing the needle shown in FIG. 7;

FIG. 11 is a sectional view taken on the line XI—XI in FIG. 10; and

FIG. 12 is a sectional view taken on the line XII—XII in FIG. 9.

Figure 1:
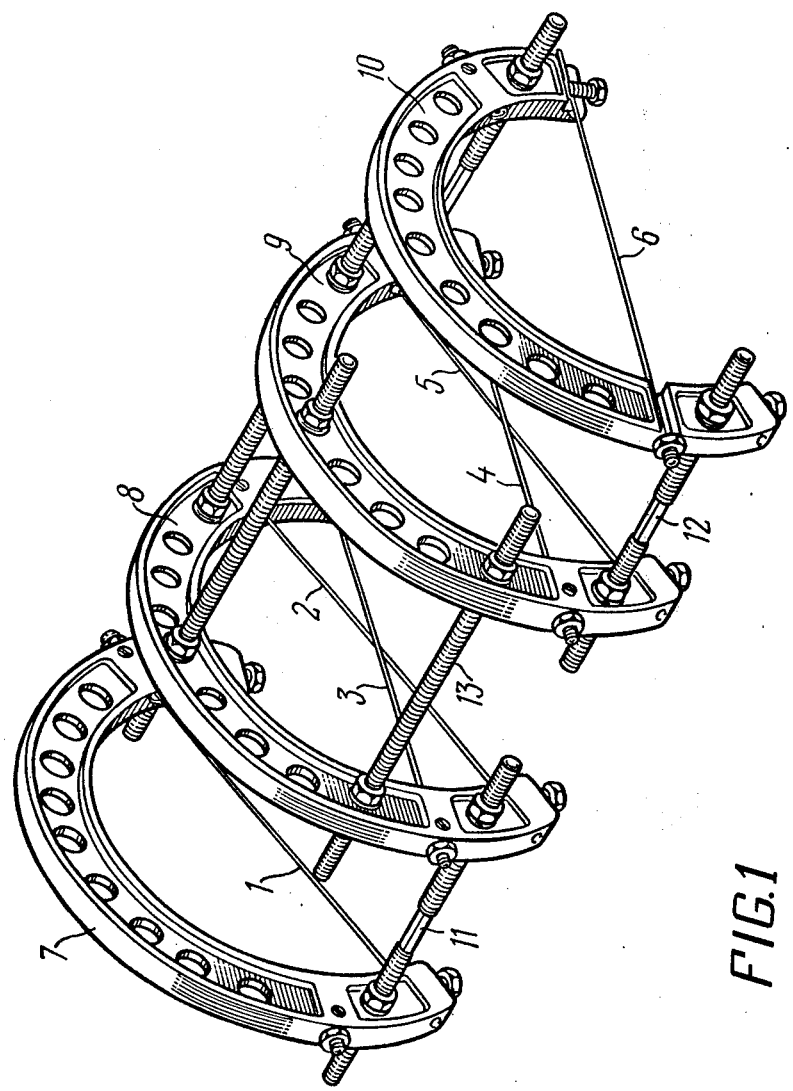
FIG. 1 is a schematic general view of a surgical apparatus for external transosteal fixation of bone fragments and joint ends, in accordance with the invention.

As an example of realization of the present invention, the following describes a surgical apparatus for external transosteal fixation of bone fragments.

Referring now to the drawings, the proposed apparatus comprises needles 1, 2 and 3 (FIG. 1) to be driven through one of the bone fragments being aligned, and needles 4, 5 and 6 to be driven through the other bone fragment. The needle 1 is secured in a brace 7; the needles 2 and 3 in a brace 8; the needles 4 and 5 in a brace 9; and the needle 6 in a brace 10.

The braces 7 and 8 are rigidly interconnected by two tie bolts 11 to form a rigid system with the needles 1, 2 and 3, said rigid system being secured on one of the bone fragments being aligned, whereas the braces 9 and 10 are rigidly interconnected by two tie bolts 12 to form a second rigid system with the needles 4, 5 and 6, said second rigid system being secured on the other bone fragment.

The two rigid systems are interconnected by means of distractors 13 which permit varying the distance between the rigid systems and hence between the bone fragments secured therein. Each needle is secured at one end in the respective brace with the aid of a clamp bolt 14 (FIG. 2), as for instance the needle 2 or 3 in the brace 8, while at the other end it is secured with the aid of a means for fixing and tightening needles. Said means comprises a drive screw 15 (FIGS. 2 and 3) which cooperates with a turn-buckle nut 16 (FIG. 2). The drive screw 15 is accommodated in a respective seat formed in the brace 8. The drive screw 15 has a flat 17 (FIGS. 3 and 4) cooperating with a set screw 18 (FIGS. 2 and 5) which prevents the drive screw 15 from turning in the seat of the brace 8. A through axial hole 19 (FIG. 3) is formed in the drive screw 15, wherethrough is extended one of the needles, e.g. the needle 3 (FIG. 6), the needle 3 being provided with a bulge 20 of cylindrical shape exceeding in diameter the axial hole 19 (FIG. 3), thereby enabling the needle 2 (FIG. 2) to be secured in the drive screw 15. The bulge on the tip of the needle may be formed as two lateral projections, as for instance bulge 21 (FIGS. 7 and 8) of needle 22. In such a case drive screw 23 (FIG. 9) must have an axial hole 24 (FIGS. 10 and 11) provided with through side slots 25 corresponding in shape and cross-sectional dimension to lateral projections 26 (FIG. 8) of the needle 22. Then, while fixing the needle 22, the latter may be extended, bulge 21 first, through the axial hole 24 (FIG. 12) and then turned through 90° so that its projections 26 prevent the needle 22 from slipping out of the axial hole 24. This arrangement is particularly valuable in those cases where part of the apparatus must be removed in the course of therapy, leaving the needles in place, for surgical intervention on the limb, with the removed portion of the apparatus reapplied or replaced by another one after the surgery. The seat for the drive screw in the brace may be so formed that the turn-buckle nut is recessed, as is the case with the turn-buckle nut 16 (FIG. 9) cooperating with the drive screw 23 which is accommodated in seat 27 formed in the brace 8.

The proposed surgical apparatus for external transosteal fixation of bone fragments and joint ends functions as follows.

The needles 1, 2 and 3 (FIG. 1) are driven through one of the bone fragments to be aligned, said needles being tightened and fixed in the braces 7 and 8, respectively. The other three needles 4, 5 and 6 are driven through the other bone fragment, tightened and fixed in the braces 9 and 10.

The needles are tightened and fixed in the apparatus in the following manner. Prior to driving the needle, e.g. the needle 2, through the bone, the points of ingress and egress of the needle 2 are marked on the limb. This completed, the hole of the drive screw 15 (FIG. 2) is brought close to the point of ingress. Then the sharp tip of the needle 2 is extended from the drill and brought to rest against the point of needle ingress, while the opening for the needle 2 in the opposite end of the brace 8 is brought in alignment with the point of egress. Then the drill is set to the working position, and the needle 2 is driven thereby through the bone like a boring bit. After the opposite sharp tip of the needle 2 is extended through the opening in the brace 8, the latter tip of the needle 2 is securely fixed with the aid of the clamp bolt 14. Then, by turning the turn-buckle nut 16, the needle 2 now fixed at both ends is tightened. While the needle 2 is driven through the limb, the brace 8 functions as a guide for the needle 2, ensuring that the needle 2 passes through the two preselected points marked on the limb.

In the course of therapy, the needle is retightened as required to maintain an optimal degree of tension essential to a successful bone union.

Thus, the permanent turn-buckle nut 16 affords the simplest possible means of correcting the needle tension at any time as prescribed by the doctor.

All this permits considerably reducing the time of treatment of injuries and diseases of bones and joints.

The needle 22 (FIG. 7) is tightened and fixed with the aid of the drive screw 23 with the axial hole 24 (FIG. 11) provided with side slots in the following manner. After the needle 22 (FIG. 7) has been driven through the bone, the sharp tip of the needle 22 is fixed by means of a clamp bolt, whereupon the bulged tip of the needle 22 is led into the seat of the brace 8 and a drive screw 23 is fitted thereon. Then the drive screw 23 is turned through 90° and fixed with the aid of a set screw similar to the set screw 18 (FIG. 5), so that the needle 22 (FIG. 12) is securely fixed in the drive screw 23. Then the needle 22 is tightened by turning the turn-buckle nut 16 (FIG. 9).

Thus, the proposed apparatus provides for a gradual and proportioned tightening and secure fixation of the needle by the simplest procedure possible, increasing the degree of spatially rigid fixation of the bones in the apparatus, which is instrumental in cutting down on therapy times and preventing invalidism.

Thus, according to the invention the surgical apparatus for external transosteal fixation of bone fragments and joint ends includes a needle to be driven through a bone, with this needle having at one end region a relatively sharp tip and at an opposed end region a bulged portion the cross-sectional area of which is greater than the cross-sectional area of the remainder of the needle. A brace has diametrically opposed portions respectively formed with bores which respectively receive the above end regions of the needle. The brace carries a screw means 14 which serves to fix the one end region of the needle which has the sharp tip in the bore of the brace in which it is received. An axially bored drive screw extends into the other bore of the brace, and the other end region of the needle which has the bulged portion extends into the axial bore of the drive screw. This axial bore of the drive screw is provided intermediate its ends with a shoulder which is directed away from the end region of the needle which has the relatively sharp tip, and the bulged portion of the needle is seated against this shoulder. The drive screw has an external thread on which there is threaded a nut which presses against the brace in the manner urging the drive screw away from the end region of the needle which has the sharp tip, so that the shoulder of the axial bore presses against the bulged portion of the needle to maintain the latter under tension. The drive screw has an exterior flat surface portion engaged by a set screw carried by the brace so as to prevent turning of the drive screw. The axial bore of the drive screw can have at the side of the shoulder which is more distant from the sharp tip of the needle a diameter larger than the remainder of this axial bore so that the needle is first introduced at its end region which has the sharp tip through the drive screw to extend through and beyond the latter until the bulged portion engages the shoulder, as indicated in the embodiment of FIGS. 3 and 6, or the bulged portion of the needle takes the form of at least one lateral projection capable of passing first through a lateral groove extension of the axial bore of the drive screw at the side of the shoulder of the axial bore which is nearer to the relatively sharp tip of the needle with the needle and drive screw being capable of turning one with respect to the other to a position where the lateral projection is out of alignment with the groove extension 25, for example, as shown in FIG. 11, so that in this way the lateral projection of the needle will engage the shoulder of the axial bore.

What is claimed is:

1. In a surgical apparatus for external transosteal fixation of bone fragments and joint ends, a needle to be driven through a bone, said needle having at one end region a relatively sharp tip and at an opposed end region a bulged portion the cross-sectional area of which is greater than the cross-sectional area of the remainder of the needle, a brace having diametrically opposed portions respectively formed with bores which respectively receive said end regions of said needle, said brace carrying at its bore which receives said one end region of the needle which has said relatively sharp tip a screw means which fixes said needle at said one end region thereof to said brace, an axially bored drive screw extending into the bore of the brace which receives the opposed end region of the needle which has the bulged portion, said opposed end region of the needle extending into the axially bored drive screw, and the latter having in its axial bore a shoulder directed away from the relatively sharp tip of the needle and against which the bulged portion of the needle is seated, said drive screw having an external flat and said brace carrying a set screw engaging said flat to prevent turning of said drive screw, and said drive screw having an external thread, and a nut threaded onto said external thread of said drive screw and cooperating with said brace for urging said drive screw away from said relatively sharp tip of the needle to press the shoulder in the axial bore of the drive screw against said bulged portion of the needle to maintain the latter under tension.

2. The combination of claim 1 and wherein said axial bore of said drive screw has at the side of said shoulder thereof which is more distant from the relatively sharp tip of the needle than the remainder of said axial bore of said drive screw a diameter greater than the remainder of the axial bore of the drive screw so that the needle must first be introduced through the axial bore of the drive screw before the relatively sharp tip of the needle is received in the bore of the brace which receives the end region of the needle which has said relatively sharp tip.

3. The combination of claim 1 and wherein the bulged portion of the needle includes a lateral projection while the axial bore of the drive screw is formed between the shoulder of the axial bore and the end of the drive screw which is nearest to the relatively sharp tip of the needle with a groove extension through which the lateral projection of the needle can pass and the groove extension of said axial bore of said drive screw and the lateral projection being angularly out of alignment with said lateral projection engaging said shoulder.

4. The combination of claim 1 and wherein the surgical apparatus includes a plurality of said braces each carrying at least one of said needles, and distractors interconnecting said braces for positioning said braces with said needles secured thereto in a desired manner.

* * * * *